US012806318B2

(12) United States Patent
Chen et al.

(10) Patent No.: US 12,806,318 B2
(45) Date of Patent: Nov. 24, 2026

(54) USE OF FERRITE MATERIALS FOR RF-INDUCED HEATING REDUCTION OF MEDICAL DEVICES

(71) Applicant: UNIVERSITY OF HOUSTON SYSTEM, Houston, TX (US)

(72) Inventors: Ji Chen, Houston, TX (US); Jianfeng Zheng, Houston, TX (US)

(73) Assignee: University of Houston System, Houston, TX (US)

( * ) Notice: Subject to any disclaimer, the term of this patent is extended or adjusted under 35 U.S.C. 154(b) by 636 days.

(21) Appl. No.: 18/118,359

(22) Filed: Mar. 7, 2023

(65) Prior Publication Data

US 2023/0293783 A1 Sep. 21, 2023

Related U.S. Application Data

(60) Provisional application No. 63/317,882, filed on Mar. 8, 2022, provisional application No. 63/317,417, filed on Mar. 7, 2022.

(51) Int. Cl.
*A61L 31/08* (2006.01)
*A61L 31/14* (2006.01)

(52) U.S. Cl.
CPC ............. *A61L 31/088* (2013.01); *A61L 31/14* (2013.01); *A61L 2400/00* (2013.01); *A61L 2420/06* (2013.01)

(58) Field of Classification Search
CPC ... A61B 17/164; A61B 17/72; A61B 17/7216; A61B 17/7225; A61B 17/74; A61B 17/744; A61B 17/60–17/666
See application file for complete search history.

(56) References Cited

U.S. PATENT DOCUMENTS 5,433,720 A * 7/1995 Faccioli ................. A61B 17/80 606/98
7,174,219 B2 2/2007 Wahlstrand et al.
(Continued)

FOREIGN PATENT DOCUMENTS

WO WO-02094113 A1 * 11/2002 ......... A61B 17/7216

OTHER PUBLICATIONS

Herrington T, et al. Construction and modeling of a reconfigurable MRI coil for lowering SAR in patients with deep brain stimulation implants. Neuroimage. 2017; 147: 577-588.
(Continued)

*Primary Examiner* — Eduardo C Robert
*Assistant Examiner* — Holly Joanna Lane
(74) *Attorney, Agent, or Firm* — Farhang Amini; Shackelford, McKinley & Norton, LLP

(57) ABSTRACT

Embodiments of the present disclosure pertain to implantable medical devices that are operational for mitigating radiofrequency (RF)-induced heating. The implantable medical devices generally include a ferrite material that is associated with at least one component of the implantable medical device and operational to reduce the RF-induced heating of the implantable medical device. Additional embodiments of the present disclosure pertain to methods of mitigating radiofrequency (RF)-induced heating of an implantable medical device by applying a ferrite material to at least one component of the implantable medical device. Thereafter, the ferrite material reduces the RF-induced heating of the medical device. In some embodiments, the methods of the present disclosure also include a step of implanting the implantable medical device into a subject, such as a human being.

26 Claims, 13 Drawing Sheets

(56) References Cited

U.S. PATENT DOCUMENTS

| | | | | |
|---|---|---|---|---|
| 7,527,626 | B2 | 5/2009 | Lutz et al. | |
| 7,853,332 | B2 | 12/2010 | Olsen et al. | |
| 8,055,351 | B2 | 11/2011 | Atalar et al. | |
| 8,145,324 | B1 | 3/2012 | Stevenson et al. | |
| 8,255,054 | B2 | 8/2012 | Denker et al. | |
| 8,319,496 | B2 | 11/2012 | Eryaman et al. | |
| 8,433,421 | B2 | 4/2013 | Atalar et al. | |
| 8,550,979 | B2 | 10/2013 | Witzmann et al. | |
| 8,903,505 | B2 | 12/2014 | Stevenson et al. | |
| 9,192,393 | B2 | 11/2015 | Piferi et al. | |
| 9,233,240 | B2 | 1/2016 | Min et al. | |
| 9,248,283 | B2 | 2/2016 | Halperin et al. | |
| 9,492,651 | B2 | 11/2016 | Bottomley et al. | |
| 9,622,780 | B2 | 4/2017 | Gerold et al. | |
| 10,219,834 | B2 | 3/2019 | Chen et al. | |
| 10,335,590 | B2 | 7/2019 | Katnani et al. | |
| 10,488,475 | B2 | 11/2019 | Ha et al. | |
| 11,104,758 | B2 * | 8/2021 | Klun | B33Y 70/00 |
| 11,266,444 | B2 | 3/2022 | Chen et al. | |
| 2003/0144720 | A1 | 7/2003 | Villaseca et al. | |
| 2003/0163187 | A1 | 8/2003 | Weber et al. | |
| 2005/0107870 | A1 | 5/2005 | Wang et al. | |
| 2006/0173285 | A1 | 8/2006 | Mallozzi et al. | |
| 2007/0083244 | A1 | 4/2007 | Stevenson et al. | |
| 2008/0051854 | A1 | 2/2008 | Bulkes et al. | |
| 2008/0108995 | A1 * | 5/2008 | Conway | A61B 17/7216 606/63 |
| 2009/0270956 | A1 | 10/2009 | Vase et al. | |
| 2009/0287212 | A1 * | 11/2009 | Hirata | A61B 17/645 606/59 |
| 2014/0052134 | A1 * | 2/2014 | Orisek | A61B 17/7216 606/63 |
| 2015/0297886 | A1 | 10/2015 | Stone et al. | |
| 2019/0092848 | A1 * | 3/2019 | Jones | A61P 19/10 |
| 2021/0205589 | A1 * | 7/2021 | Dong | A61M 27/002 |

OTHER PUBLICATIONS

McElcheran CE, Yang B, Anderson KJT, Golenstani-Rad L, and Graham SJ. Investigation of parallel radiofrequency transmission for the reduction of heating in long conductive leads in 3 Tesla magnetic resonance imaging. PLoS One. 2015; 10:1-21.

Eryaman Y, Turk EA, Oto C, Algin O, and Atalar E. Reduction of the radiofrequency heating of metallic devices using a dual-drive birdcage coil. Magn Reson Med. 2013; 69: 845-852.

Eryaman Y, Akin B, and Atalar E. Reduction of implant RF heating through modification of transmit coil electric field. Magn Reson Med. 2011; 65: 1305-1313.

Golestanirad L, et al. Reconfigurable MRI coil technology can substantially reduce RF heating of deep brain stimulation implants: First in-vitro study of RF heating reduction in bilateral DBS leads at 1.5 T. PLoS One. 2019; 14: 1-17.

Golestanirad L, Keil B, Angelone L. M, Bonmassar G, Mareyam A, and Wald LL. Feasibility of using linearly polarized rotating birdcage transmitters and close-fitting receive arrays in MRI to reduce SAR in the vicinity of deep brain simulation implants. Magn Reson Med. 2017; 77: 1701-1712.

Yeung CJ, Karmarkar P, and Mcveigh ER, Minimizing RF heating of conducting wires in MRI. Magn Reson Med. 2007; 58: 1028-1034.

Golestanirad L, et al. RF-induced heating in tissue near bilateral DBS implants during MRI at 1.50□ and 3T: The role of surgical lead management. Neuroimage. 2019; 184: 566-576.

Nordbeck P, et al. Measuring RF-induced currents inside implants: Impact of device configuration on MRI safety of cardiac pacemaker leads. Magn Reson Med. 2007; 61: 570-578.

Nyenhuis JA, Park SM, Kamondetdacha R, Amjad A, Shellock FG, and Rezai Ar, MRI and implanted medical devices: Basic interactions with an emphasis on heating. IEEE Trans Device Mater Reliab. 2005; 5: 467-479.

Golestanirad L, Angelone LM, Iacono MI, Katnani H, Wald LL, and Bonmassar G. Local SAR near deep brain stimulation (DBS) electrodes at 64 and 127 MHz: A simulation study of the effect of extracranial loops. Magn Reson Med.2017; 78: 1558-1565.

Baker KB, Tkach J, Hall JD, Nyenhuis JA, Shellock FG, and Rezai AR. Reduction of magnetic resonance imaging-related heating in deep brain stimulation leads using a lead management device. Neurosurgery. 2005; 57: 392-397.

Mattei E, et al. Complexity of MRI induced heating on metallic leads: Experimental measurements of 374 configurations. BioMed Eng OnLine. 2008;7: 11.

Nordbeck P, et al. Spatial distribution of RF-induced E-fields and implant heating in MRI. Magn Reson Med. 2008; 60: 312-319.

Yang R, Zheng J, Wang Y, Guo R, Kainz W, and Chen J. An Absorbing Radio Frequency Shield to Reduce RF Heating Induced by Deep Brain Stimulator During 1.5-T MRI. IEEE Trans Electromagn Compat. 2019; 61: 1726-1732.

Corcoles J, Zastrow E, and Kuster N. Optimization-based strategy in multiple-channel magnetic resonance systems operating at 128 MHz to reduce radiofrequency heating induced by active implantable medical devices. In: Proceedings of the 2017 XXXIInd General Assembly and Scientific Symposium of the International Union of Radio Science (URSI GASS), Montreal, Canada; 2017: 17338812.

Zeng Q, Wang Q, Kainz W, and Chen J. Impact of RF Shimming on RF-Induced Heating Near Implantable Medical Electrodes in a 3T MRI Coil. IEEE Trans Electromagn Compat. 2020; 62: 52-64.

Córcoles J, Zastrow E, and Kuster N. Convex optimization of MRI exposure for mitigation of RF-heating from active medical implants. Phys Med Biol. 2015; 60: 7293-7308.

Bottomley P, Kumar A, Edelstein W, Allen J, and Karmarkar P. Designing passive MRI-safe implantable conducting leads with electrodes. Med Phys.37: 3828-3843.

Wang Y, Zheng J, Guo R, Wang Q, Kainz W, Long S, Chen J. A technique for the reduction of RF-induced heating of active implantable medical devices during MRI. Magn Reson Med. Jan. 2022;87(1):349-364. doi: 10.1002/mrm.28953. Epub Aug. 10, 2021. PMID: 34374457.

Nordbeck P, et al. Reducing RF-related heating of cardiac pacemaker leads in MRI: Implementation and experimental verification of practical design changes, Magn Reson Med. 2012; 68: 1963-1972.

Gray RW, Bibens WT, and Shellock FG. Simple design changes to wires to substantially reduce MRI-induced heating at 1.5 T: Implications for implanted leads. Magn Reson Imaging. 2005; 23: 887-891.

McCabe SO, and Scott JB. Cause and Amelioration of MRI-Induced Heating Through Medical Implant Lead Wires. In: Proceedings of the 21st Electronics New Zealand Conference. Hamilton, New Zealand; 2014.

McCabe S, Scott J, and Butler S. Electromagnetic techniques to minimize the risk of hazardous local heating around medical implant electrodes during MRI scanning. In: Proceedings of the 2015 European Microwave Conference (EuMC), Paris, France; 2015: 15649231.

Zheng C, Chen X, Nguyen BT, Sanpitak P, Vu J, Bagci U, Golestanirad L. Predicting RF Heating of Conductive Leads During Magnetic Resonance Imaging at 1.5 T: A Machine Learning Approach. Annu Int Conf IEEE Eng Med Biol Soc. Nov. 2021;2021:4204-4208. doi: 10.1109/EMBC46164.2021.9630718. PMID: 34892151; PMCID: PMC9940641.

Kazemivalipour E, Bhusal B, Vu J, Lin S, Nguyen BT, Kirsch J, Nowac E, Pilitsis J, Rosenow J, Atalar E, Golestanirad L. Vertical open-bore MRI scanners generate significantly less radiofrequency heating around implanted leads: A study of deep brain stimulation implants in 1.2T OASIS scanners versus 1.5T horizontal systems. Magn Reson Med. Sep. 2021;86(3):1560-1572. doi: 10.1002/mrm.28818. Epub May 7, 2021. PMID: 33961301; PMCID: PMC8713475.

Golestanirad L, Angelone LM, Kirsch J, Downs S, Keil B, Bonmassar G, Wald LL. Reducing RF-induced Heating near Implanted Leads through High-Dielectric Capacitive Bleeding of Current (CBLOC). IEEE Trans Microw Theory Tech. Mar. 2019;67(3):1265-1273. doi: 10.1109/TMTT.2018.2885517. Epub Jan. 1, 2019. PMID: 31607756; PMCID: PMC6788634.

(56) References Cited

OTHER PUBLICATIONS

J Wooldridge et al., Gradient coil and radiofrequency induced heating of orthopaedic implants in MRI: influencing factors , 2021 Phys. Med. Biol. 66 245024.
Addevico et al., Magnetic Resonance Imaging of the Knee in the Presence of Bridging External Fixation: A Comparative Experimental Evaluation of Four External Fixators, Including Dolphi, J. Funct. Morphol. Kinesiol. 2022, 7, 4. https://doi.org/10.3390/jfmk701000.
Elsissy P, Akpolat YT, Chien A, Cheng WK. MRI evaluation of the knee with non-ferromagnetic external fixators: cadaveric knee model. Eur J Orthop Surg Traumatol. Jul. 2015;25(5):933-9. doi: 10.1007/s00590-015-1655-9. Epub Jun. 9, 2015. PMID: 26051439.
Massimo Max Morandi, Alberto Simoncini, Claire Hays, John Garrett, R. Shane Barton, Andreas Chen, Giovanni F. Solitro, Optimal configuration for stability and magnetic resonance imaging quality in temporary external fixation of tibial plateau fractures, Orthopaedics & Traumatology: Surgery & Research, vol. 106, Issue 7, 2020, pp. 1405-1412, ISSN 1877-0568,.
Ryan S, Moon AS, Gordon M, Flacke S, Soni S, Salzler MJ, Stelma S, Marcantonio A. External Fixation Devices Within the Magnetic Resonance Imaging Bore: A Safety and Radiologic Analysis. J Orthop Trauma. Jan. 1, 2021;35(1): e25-e30. doi: 10.1097/BOT.0000000000001848. PMID: 32482974.
Y. Liu, J. Shen, W. Kainz, S. Qian, W. Wu and J. Chen, "Computational study of external fixation devices surface heating in MRI RF environment," 2012 IEEE International Symposium on Electromagnetic Compatibility, Pittsburgh, PA, USA, 2012, pp. 612-616, doi: 10.1109/ISEMC.2012.6351691.
Acikel V, Uslubas A and Atalar E 2015 Modeling of electrodes and implantable pulse generator cases for the analysis of implant tip heating under MR imaging Med. Phys. 42 3922-31.
Baker K B, Tkach JA, Phillips M D and Rezai A R 2006 Variability in RF-induced heating of a deep brain stimulation implant across MR systems J. Magn. Reson. Imaging 24 1236-42.
Calcagnini G, Triventi M, Censi F, Mattei E, Bartolini P, Kainz W and Bassen H I 2008 In vitro investigation of pacemaker lead heating induced by magnetic resonance imaging: Role of implant geometry J. Magn. Reson. Imaging 28 879-86.
Ladd ME, and Quick HH. Reduction of resonant RF heating in intravascular catheters using coaxial chokes. Magn Reson Med. 2000; 43: 615-619.
Mccabe S, and Scott J. A novel implant electrode design safe in the RF Field of MRI Scanners. IEEE Trans Microw Theory Tech. 2017; 65: 3541-3547.
Golestanirad L, et al. Reducing RF-Induced Heating Near Implanted Leads Through High-Dielectric Capacitive Bleeding of Current (CBLOC). IEEE Trans Microw Theory Tech. 2019; 67: 1265-1273.
Das R, and Yoo H. RF Heating Study of a New Medical Implant Lead for 1.5 T, 3 T, and 7 T MRI Systems. IEEE Trans. Electromagn Compat. 2016; 59: 360-366.
Yang R, Zheng J, Wang Y, Guo R, Kainz W, and Chen J. Impact of electrode structure on rf-induced heating for an aimd implanted lead in a 1.5-Tesla mri system. IEEE J Electromagn, RF, Microw Med Biol. 2019; 3: 247-253.
Liu J, Jackson DR, Wang Q, Kainz W, and Chen J. On the Relationship Between Impedances of Active Implantable Medical Devices and Device Safety Under MRI RF Emission. IEEE Trans Electromagn Compat. 2019. doi: 10.1109/TEMC.2019.2938908.
Serano P, Angelone LM, Katnani H, Eskandar E, and Bonmassar G. A novel brain stimulation technology provides compatibility with MRI. Sci. Rep. 2015; 5: 1-10.
Wang Y, Zheng J, Wang Q, Chen J. A counterpoise design for RF-induced heating reduction. In: Proceedings of the 2020 42nd Annual International Conference of the IEEE Engineering in Medicine & Biology Society (EMBC). Montreal, Canada. 2020; 19963937.
Liu J, Zheng J, Wang Q, Kainz W, and Chen J. A Transmission Line Model for the Evaluation of MRI RF-Induced Fields on Active Implantable Medical Devices. IEEE Trans Microw Theory Tech. 2018; 66: 4271-4281.
Wang Z, Zheng J, Wang Y, Kainz W, and Chen J. On the Model Validation of Active Implantable Medical Device for MRI Safety Assessment. IEEE Trans Microw Theory Tech. 2020; 68: 2234-2242.
Feng S, Qiang R, Kainz W, and Chen J. A technique to evaluate MRI-induced electric fields at the ends of practical implanted lead. IEEE Trans Microw Theory Tech. 2015; 63: 305-313.
Iso T. 10974: Assessment of the safety of magnetic resonance imaging for patients with an active implantable medical device. Geneva, Switzerland: International Organization for Standardization; 2012.
Wang Y, et al. A Novel Device Model Validation Strategy for 1.5 T and 3 T MRI Heating Safety Assessment. IEEE Trans Instrum Meas. 2020; 69: 6381-638.
Wang Y, et al. On the development of equivalent medium for active implantable device radiofrequency safety assessment. Magn Reson Med. 2019; 82:1164-1176.
Dichtl C, Sippel P and Krohns S 2017 Dielectric Properties of 3D Printed Polylactic Acid Adv. Mater. Sci. Eng. 2017.
Erhardt J B, Fuhrer E, Gruschke O G, Leupold J, Wapler M C, Hennig J, Stieglitz T and Korvink J G 2018 Should patients with brain implants undergo MRI? J. Neural Eng. 15.
Huang X, Zheng J, Wu X, Kono M, Hozono H, Kainz W, Yang F and Chen J 2015 MRI Heating Reduction for External Fixation Devices Using Absorption Material IEEE Trans. Electromagn. Compat. 57 635-42.
Liu Y, Chen J, Shellock F G and Kainz W 2013 Computational and experimental studies of an orthopedic implant: MRI-related heating at 1.5-T/64-MHz and 3-T/128-MHz J. Magn. Reson. Imaging 37 491-7.
Liu Y, Kainz W, Qian S, Wu W and Chen J 2014 Effect of insulating layer material on RF-induced heating for external fixation system in 1.5 T MRI system Electromagn. Biol. Med. 33 223-7.
Luechinger R, Boesiger P and Disegi J A 2006 Safety Evaluation of Large External Fixation Clamps and Frames in a Magnetic Resonance Environment 17-22.
Missoffe A, Kabil J, Vuissoz P A and Felblinger J 2018 Transmission line model of an implanted insulated cable for magnetic resonance imaging radiofrequency hazard evaluation IEEE J. Electromagn. RF Microwaves Med. Biol. 2 201-7.
Mohsin S A, Sheikh N M and Saeed U 2008 MRI-induced heating of deep brain stimulation leads Phys. Med. Biol. 53 5745-56.
Rezai A R, Finelli D, Nyenhuis J A, Hrdlicka G, Tkach J, Sharan A, Rugieri P, Stypulkowski P H and Shellock F G 2002 Neurostimulation systems for deep brain stimulation: In vitro evaluation of magnetic resonance imaging-related heating at 1.5 Tesla J. Magn. Reson. Imaging 15 241-50.
Shellock F C and Crues J V. 2004 MR procedures: Biologic effects, safety, and patient care Radiology 232 635-52.
Shellock F G, Woods T O and Crues J V. 2009 MR labeling information for implants and devices: Explanation of terminology Radiology 253 26-30.
Yeung C J, Susil R C and Atalar E 2002 RF safety of wires in interventional MRI: Using a safety index Magn. Reson. Med. 47 187-93.
Zeng Q, Wang Q, Zheng J, Kainz W and Chen J 2018 Evaluation of MRI RF electromagnetic field induced heating near leads of cochlear implants Phys. Med. Biol. 63.
International Search Report for PCT/US2023/014687, mailed on Jun. 26, 2023.

* cited by examiner

USE OF FERRITE MATERIALS FOR RF-INDUCED HEATING REDUCTION OF MEDICAL DEVICES

CROSS-REFERENCE TO RELATED APPLICATIONS

The present application claims the benefit of U.S. Provisional Patent Application No. 63/317,417, filed on Mar. 7, 2022 and U.S. Provisional Patent Application No. 63/317,882, filed on Mar. 8, 2022. The entirety of each of the aforementioned applications is incorporated herein by reference.

STATEMENT REGARDING FEDERALLY SPONSORED RESEARCH

This invention was made with government support under Grant No. 1922389, awarded by the National Science Foundation. The government has certain rights in the invention.

BACKGROUND

Radiofrequency (RF)-induced heating of implantable medical device components, such as the electrodes of active implantable medical devices (AIMDs) and screw tips of external fixation medical devices, is the limiting factor for a safe MRI scan. In fact, many implantable medical devices are prohibited from MRI scans or scanned under restricted conditions due to such RF-induced heating. Furthermore, the re-engineering or re-design of implantable medical device components for RF-induced heating reduction are not feasible due to mechanical requirements. Numerous embodiments of the present disclosure aim to address these limitations.

SUMMARY

Embodiments of the present disclosure pertain to implantable medical devices that are operational for mitigating radiofrequency (RF)-induced heating. The implantable medical devices of the present disclosure generally include a ferrite material that is associated with at least one component of the implantable medical device and operational to reduce the RF-induced heating of the implantable medical device.

Additional embodiments of the present disclosure pertain to methods of mitigating radiofrequency (RF)-induced heating of an implantable medical device by applying a ferrite material to at least one component of the implantable medical device. Thereafter, the ferrite material reduces the RF-induced heating of the medical device. In some embodiments, the methods of the present disclosure also include a step of implanting the implantable medical device into a subject, such as a human being.

DESCRIPTION OF THE DRAWINGS

FIG. 2A shows the placement of a single ferrite bead near the middle of an AIMD leads body. FIG. 2B shows the placement of a second ferrite bead near the proximal end of the AIMD. FIG. 2C shows the placement of ferrite beads around 5 cm from the AIMD distal end. FIG. 2D shows the placement of ferrite beads around 10 cm from the AIMD distal end.

FIGS. 3A and 3B show comparisons of transfer function models of AIMDs with and without ferrite materials at 1.5 T (FIG. 3A) and 3T (FIG. 3B). The "Mid ferrite" and "Mid & Proximal ferrite" AIMDs represent the AIMDs in FIGS. 2A and 2B, respectively. FIGS. 3C and 3D show comparisons of transfer function models of AIMDs with and without ferrite materials at 1.5 T (FIG. 3C) and 3 T (FIG. 3D). The "5 cm Pos ferrite" and "10 cm Pos ferrite" legends represent the AIMDs in FIGS. 2C and 2D, respectively.

FIG. 4A shows an AIMD leads body without ferrite materials. FIG. 4B shows the placement of a ferrite bead at about 11 cm from the distal tip. FIG. 4C shows the placement of ferrite beads at about 11 cm and 21 cm from the distal tip.

DETAILED DESCRIPTION

Figure 1A:
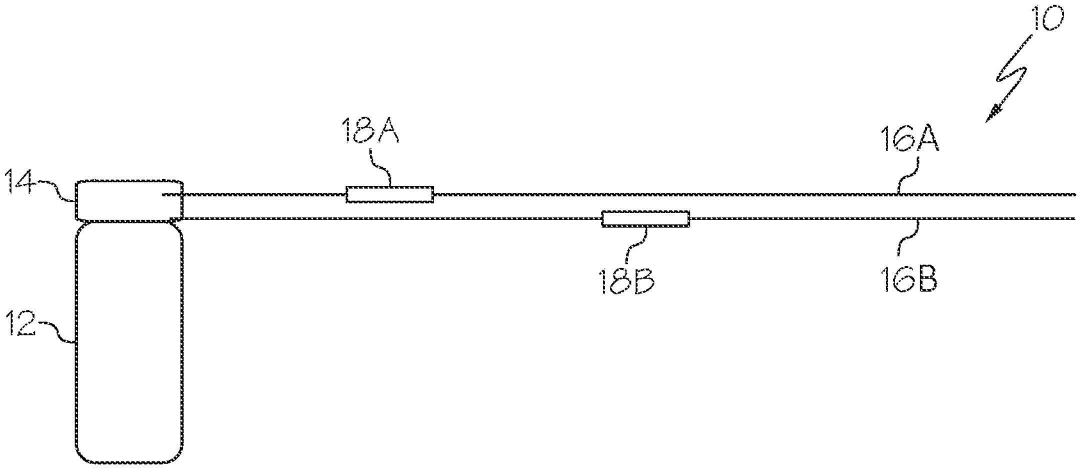
FIG. 1A depicts an active implantable medical device (AIMD) in accordance with various embodiments of the present disclosure.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Magnetic resonance imaging (MRI) has been a standard medical diagnostic tool over recent decades owing to its high-resolution imaging quality for soft tissue. Compared with X-ray or computed tomography (CT) imaging, MRI does not have ionizing radiation and long-term health risks. In fact, MRI is considered as one of the safest imaging methods in hospitals. However, patients with implantable medical devices are usually restricted from MRI because of the potential safety concerns, especially the radiofrequency (RF) induced heating generated during MRI scans.

During magnetic resonance imaging (MRI), the radiofrequency (RF)-induced heating of implantable medical devices is one of the major concerns for patient safety. For instance, in active implantable medical devices (AIMDs), the concentrated energy dissipating in the lead-tip region can lead to high local temperature rise and cause tissue damage. To mitigate RF-induced heating of AIMDs, diverse approaches have been proposed in the literature. These methods can be divided into two classes.

The approaches in the first class have focused on reducing the strength of the incident electric (E)-fields in the device region by a) changing the construction of the transmit RF coil, b) selecting appropriate implantation trajectories of AIMDs in patients, c) using absorbing radio frequency shields, and d) applying RF-shimming techniques. The approaches in the second class have relied on modifications of the AIMDs to achieve heating reduction. These approaches have included a) increasing the RF resistance of the lead body with appropriate winding techniques, b) introducing band-stop filters or coaxial chokes on the lead body near the lead-tip, c) adding an external wire to the AIMD lead, d) introducing high-dielectric materials in the lead design to dissipate the induced energy along the lead body into the surrounding tissues, e) enlarging the electrode to reduce the energy density, f) adding lumped elements to change the termination impedance, and g) introducing a resistive-tapered strip line at the lead-tip.

The aforementioned approaches have made significant progress toward AIMD safety. However, most studies have only considered a limited number of in-vitro cases without evaluating the heating associated with clinically relevant in-vivo scenarios. Furthermore, the re-engineering or re-design of AIMD leads for RF-induced heating reduction may not always be feasible due to mechanical requirements.

External fixation medical devices are another type of implantable medical devices that can cause a severe heating concern during MRI scans. External fixation medical devices are surgical devices that may be used to stabilize fractured bones. A typical external fixation medical device generally includes three parts: 1) fixators (e.g., metallic pins or wires) to be screwed into the fractured bones, 2) a base area (e.g., rods or bars made of carbon fiber or metallic materials) to anchor (e.g., bridge) the fixators, and 3) securing mechanisms (e.g., metallic clamps) to connect the fixators to the base area (e.g., rods). Compared with other passive implants, the base area (e.g., rods) and securing mechanisms (e.g., clamps) are outside the human body and thus are much closer to the RF coils.

It has been observed that external fixation medical devices often experience a higher heating effect than that of fully implanted passive devices. For instance, it has been shown that external fixation devices can cause a high local peak specific absorption rate over 1 gram (SARig) of around 800 W/kg and lead to a temperature rise of more than 50° C. in specific settings.

To mitigate the RF-induced heating of the external fixation medical devices, studies have proposed the use of insulating materials to block the transmission of the RF energy to the fixator tips. Such studies have shown that, through the application of proper insulating materials, the RF-induced heating could be reduced by 67% at 1.5 T. Other studies improved this method by changing the insulating material to absorbing materials. Such materials could further absorb part of the RF-induced energy received by the device frame, thereby reducing the heating effect in the human body.

Although previous studies achieved good results in mitigating the RF heating of external fixation medical devices, there are remaining limitations associated with these works. First, the studies only investigated the effects of the relative permittivity on the RF heating and did not consider the effects of other parameters such as the thickness of the insulating material. Second, the methods used in the studies were demonstrated at 1.5 T MRI. As high field MRI is widely used in clinical settings, there arises a need to investigate the effectiveness of the insulating and absorbing materials in reducing RF heating of the external fixation devices at 3 T MRI.

As such, a need exists to develop more effective methods of mitigating RF-induced heating of implantable medical devices, such as AIMDs and external fixation medical devices. A need also exists to utilize more effective materials to mitigate RF-induced heating in such implantable medical devices. Numerous embodiments of the present disclosure aim to address the aforementioned needs.

Medical Devices

In some embodiments, the present disclosure pertains to medical devices that are operational for mitigating radio frequency (RF)-induced heating. The medical devices of the present disclosure generally include a ferrite material that is associated with at least one component of the medical device. In some embodiments, the ferrite material is operational to reduce the RF-induced heating of the medical device.

In some embodiments, the medical devices of the present disclosure include implantable medical devices. Implantable medical devices generally refer to medical devices that can be completely or partially introduced into a tissue (e.g., cardiac tissue), organ (e.g., heart) or cavity (e.g., oral cavity) of a subject on a temporary or permanent basis. In some embodiments, implantable medical devices include, without limitation, external fixation medical devices, active implantable medical devices (AIMDs), cochlear implants, prosthetics, stents, hip implants, insulin injection patches, artificial joints, breast implants, intraocular lenses, intrauterine contraceptive devices, dental implants, or combinations thereof.

In some embodiments, the medical devices of the present disclosure include AIMDs. AIMDs generally refer to implantable medical devices that rely on artificially generated electrical energy or a power source for operation. In some embodiments, the AIMDs include, without limitation, cardiac implantable electrical devices (CIEDs), defibrillators, pacemakers, implantable cardioverter defibrillators (ICDs), cardiac resynchronization therapy (CRT) devices, CRT pacers (CRT-P), CRT defibrillators (CRTD), neuromodulation systems, deep brain stimulation systems, spinal cord stimulation systems, or combinations thereof.

In some embodiments, the implantable medical devices of the present disclosure include external fixation medical devices. External fixation medical devices generally refer to implantable medical devices that are operational to stabilize a compromised area of a body, such as a fractured bone or a strained muscle. In some embodiments, external fixation medical devices include fixators that are fully or partially implantable into a fractured area of a body, such as a fractured bone.

Ferrite Materials

The medical devices of the present disclosure may include various types of ferrite materials. In some embodiments, ferrite materials include iron oxide ($Fe_2O_3$) combined with one or more additional metallic elements. In some embodiments, the one or more metallic elements include, without limitation, iron (Fe), strontium (Sr), barium (Ba), manganese (Mn), nickel (Ni), zinc (Zn), cobalt (Co), and combinations thereof. In some embodiments, the ferrite materials include, without limitation, strontium (Sr)-containing ferrites, barium (Ba)-containing ferrites, manganese (Mn)-containing ferrites, nickel (Ni)-containing ferrites, zinc (Zn)-containing ferrites, cobalt (Co)-containing ferrites, Ni, Zn-containing ferrites, Mn, Zn-containing ferrites, magnetite ($Fe_3O_4$), $ZnFe_2O_4$, $BaFe_{12}O_{19}$ ($BaO:6Fe_2O_3$), $BaO\cdot 2(FeO)\cdot 8(Fe_2O_3)$, $SrFe_{12}O_{19}$ ($SrO:6Fe_2O_3$), $MnZnFe_2O_4$, $NiZnFe_2O_4$, $CoFe_2O_4$ ($CoO\cdot Fe_2O_3$), $Ba_2ZnFe_{18}O_{23}$, and combinations thereof. In some embodiments, the ferrite materials are operational for leading to a relative permeability that is larger than 1.

The ferrite materials of the present disclosure can be in various forms. For instance, in some embodiments, the ferrite materials of the present disclosure represent an exogenous component of a medical device. In some embodiments, the ferrite materials of the present disclosure are protruded out of at least one component of a medical device. In some embodiments, the ferrite materials of the present disclosure are in the form of one or more rings. In some embodiments, the ferrite materials of the present disclosure are in the form of one or more beads. In some embodiments, the ferrite materials of the present disclosure are in the form of one or more ferrite magnetic rings. In some embodiments, the ferrite magnetic rings include a magnetic core and an outer surface. In some embodiments, the outer surface includes a plastic outer surface.

In some embodiments, the ferrite materials of the present disclosure are in the form of composites. In some embodiments, the ferrite materials of the present disclosure are in the form of blocks.

In some embodiments, the ferrite materials of the present disclosure are in the form of a coating. In some embodiments, the ferrite materials of the present disclosure are in the form of coating layers of different thicknesses.

In some embodiments, the ferrite materials have thicknesses that range from about 0.1 mm to about 10 mm. In some embodiments, the ferrite materials have thicknesses that range from about 0.1 mm to about 0.7 mm. In some embodiments, the ferrite materials have thicknesses that range from about 0.1 mm to about 0.5 mm.

Medical Device Components Containing Ferrite Materials

Ferrite materials may be associated with various medical device components in various manners. For instance, in some embodiments, ferrite materials may be associated with an outer surface of a medical device component. In some embodiments, the medical device component includes at least one component that is partially or completely implantable into a subject. In some embodiments, the medical device component includes an electrode of an implantable medical device that is partially or completely implantable into the subject.

In some embodiments, the medical device component of an implantable medical device includes a lead body of an implantable medical device. In some embodiments, the lead body includes a lead body of an AIMD, such as a pacemaker. In some embodiments, the lead body includes a proximal end, a middle area, and a distal end. In some embodiments, the lead body is in the form of an elongated and insulated structure that includes one or more metallic inner conductors and contacting electrodes at the distal end.

The ferrite materials of the present disclosure may be associated with any locations or lengths of a lead body. For instance, in some embodiments, the ferrite material is inside the lead body. In some embodiments, the ferrite material is outside the lead body. In some embodiments, the ferrite material is at the proximal end of the lead body. In some embodiments, the ferrite material is inside the middle of the lead body. In some embodiments, the ferrite material is inside the distal end of the lead body. In some embodiments, the ferrite material may be associated 5 cm from the distal end of the lead body. In some embodiments, the ferrite material may be associated 10 cm from the distal end of the lead body.

In some embodiments, the ferrite materials of the present disclosure are associated with a fixator of an external fixation medical device. In some embodiments, the fixator is in the form of a wire. In some embodiments, the fixator is in the form of a pin. In some embodiments, the fixator includes a proximal end operational for attaching to a base area of the external fixation medical device, and a distal end operational for insertion into a subject's bone. In some embodiments, the ferrite material is associated with the proximal end of the fixator. In some embodiments, the ferrite material is associated with the distal end of the fixator.

In some embodiments, the ferrite material may be associated near the proximal end of the fixator. In some embodiments, the ferrite material may be associated 5 cm from the proximal end of the fixator. In some embodiments, the ferrite material may be associated 10 cm from the proximal end of the fixator.

In some embodiments, the ferrite materials of the present disclosure are associated with a base area of an external fixation medical device. In some embodiments, the base area is operational for anchoring a fixator. In some embodiments, the base area is in the form of a bar.

An example of a medical device of the present disclosure is illustrated in FIG. 1A as pacemaker 10, which includes an implantable pulse generator 12, header assembly 14, and a lead body that includes an outer portion 16A and an inner portion 16B. In this example, ferrite materials 18A and 18B are associated with the outer portion 16A and inner portions 16B of the lead body, respectively. Furthermore, ferrite materials 18A and 18B in this example are in the form of beads that protrude out of the lead body.

Figure 1B:
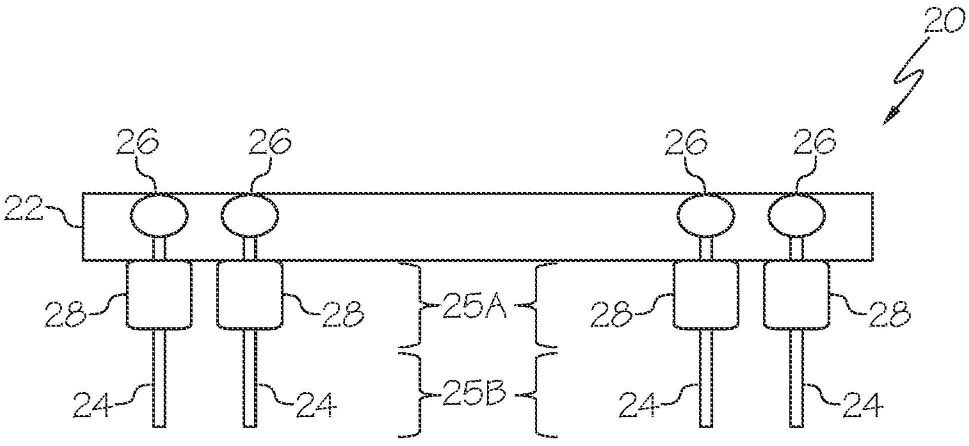
FIG. 1B depicts an external fixation medical device in accordance with various embodiments of the present disclosure.

Another example of a medical device of the present disclosure is illustrated in FIG. 1B as external fixation medical device 20, which includes a base area 22, fixators 24 operational for insertion into a subject's bone, and securing mechanisms 26 operational for securing the fixators to the base area 22. Base area 22 is generally operational for anchoring fixators 24. In some embodiments, base area 22 may be in the form of rods or bars. In some embodiments, securing mechanism 26 may be in the form of clamps. Fixators 24 include a proximal end 25A and a distal end 25B. In this example, ferrite materials 28 are associated with proximal ends 25A of fixators 24. Furthermore, ferrite materials 28 in this example are in the form of rings.

Methods of Mitigating RF-Induced Heating of Medical Devices

Figure 1C:
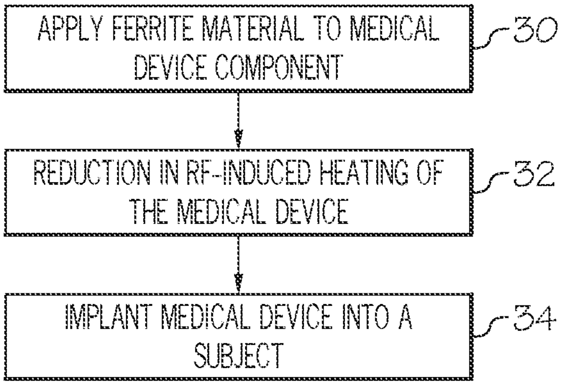
FIG. 1C illustrates a method of mitigating RF-induced heating of a medical device.

In some embodiments, the present disclosure pertains to methods of mitigating radiofrequency (RF)-induced heating of a medical device. In some embodiments illustrated in FIG. 1C, the methods of the present disclosure include: applying a ferrite material to a component of the medical device (step 30) to result in the reduction of the RF-induced heating of the medical device (step 32). In some embodiments, the methods of the present disclosure may also include a step of implanting the medical device into a subject (step 34).

As set forth in more detail herein, the methods of the present disclosure can have numerous embodiments. In particular, various ferrite materials may be applied to various components of various medical devices to result in the reduction of the RF-induced heating of the medical devices in various environments. Moreover, the medical devices may be implanted into various subjects for various purposes.

Medical Devices

The methods of the present disclosure may be utilized to apply ferrite materials to components of various medical devices. Suitable medical devices were described supra. For instance, in some embodiments, the medical devices include implantable medical devices. In some embodiments, the medical devices include external fixation medical devices. In some embodiments, the medical devices include an active implantable medical device (AIMD).

Ferrite materials may be applied to various medical device components. Suitable medical device components were also described supra. For instance, in some embodiments, the medical device component includes an implantable medical device component that is partially or completely implantable into a subject. In some embodiments, the medical device component includes an electrode of an implantable medical device that is partially or completely implantable into the subject. In some embodiments, the medical device component includes a lead body of an AIMD. In some embodiments, the medical device component includes a fixator of an external fixation medical device.

Applying of Ferrite Materials

The methods of present disclosure may apply ferrite materials to medical device components in various manners. For instance, in some embodiments, the applying occurs by spraying the ferrite materials onto the medical device components. In some embodiments, the applying occurs by inserting the ferrite materials onto the medical device components. In some embodiments, the applying occurs by placing the ferrite materials on the medical device components. In some embodiments, the applying occurs by embedding the ferrite materials onto the medical device components.

Reduction of RF-Induced Heating

The application of ferrite materials to medical device components may result in the reduction of RF-induced heating in various manners. For instance, in some embodiments, the applied ferrite material reduces RF-induced heating by blocking or minimizing the induced current from RF waves.

The application of ferrite materials to medical device components may result in the reduction of RF-induced heating in various environments. For instance, in some embodiments, the environment is an environment under magnetic resonance (MR), such as an MRI scanner. In some embodiments, the applied ferrite material mitigates RF-induced heating from a magnetic resonance (MR) RF coil. In some embodiments, the environment is an electromagnetic environment.

Implantation of Medical Device

In some embodiments, the methods of the present disclosure also include a step of implanting the medical devices of the present disclosure into a subject. In some embodiments, the subject is a human being. In some embodiments, the implantation occurs surgically.

Applications and Advantages

The methods and medical devices of the present disclosure provide numerous advantages and applications. For instance, in some embodiments, the methods and medical devices of the present disclosure can reduce RF-induced heating without requiring a redesign of medical devices (e.g., AIMD systems). Additionally, the methods and medical devices of the present disclosure can be utilized to reduce RF-induced heating of medical devices under various scenarios, such as under MRI scans. Furthermore, the methods and medical devices of the present disclosure may be applied to various implantable medical devices, such as pacemakers, implantable defibrillators, and external fixation medical devices.

ADDITIONAL EMBODIMENTS

Reference will now be made to more specific embodiments of the present disclosure and experimental results that provide support for such embodiments. However, Applicant notes that the disclosure below is for illustrative purposes only and is not intended to limit the scope of the claimed subject matter in any way.

Figure 2A:
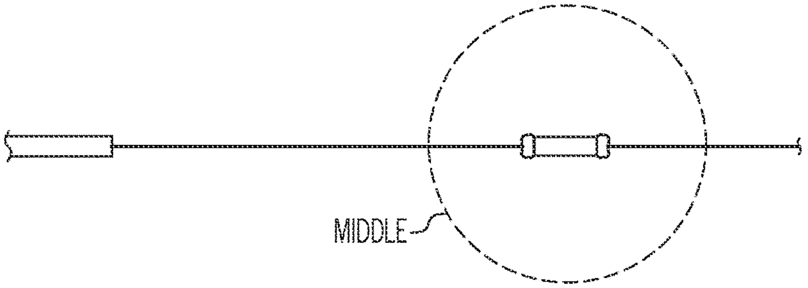
FIGS. 2A-2D illustrate the placement of ferrite materials on the leads body of an AIMD.
Figure 2B:
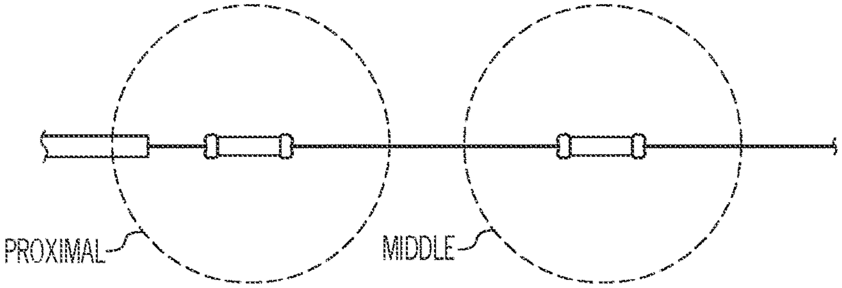
Figure 2C:
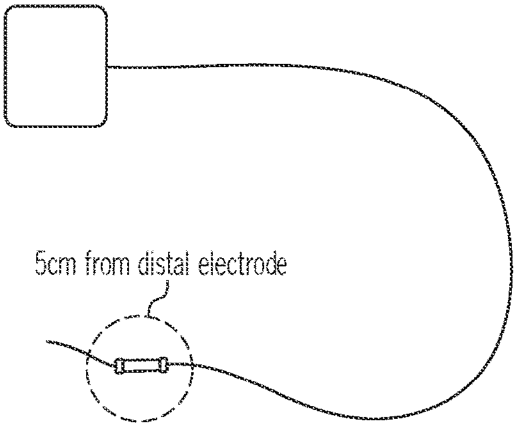
Figure 2D:
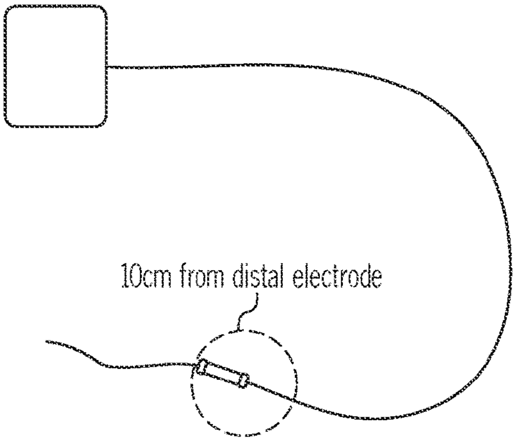

Example 1. Use of Ferrite Materials to Reduce RF-Induced Heating in Active Implantable Medical Devices This Example demonstrates the use of ferrite beads to reduce RF-induced heating in active implantable medical devices (AIMDs). Two different leads bodies, with and without the ferrite materials, were used in this Example. The device configurations are shown in FIGS. 2A-2D. Such configurations include the placement of a single ferrite bead near the middle of an AIMD leads body (FIG. 2A), the placement of a second ferrite bead near the proximal end of the AIMD leads body (FIG. 2B), the placement of ferrite beads around 5 cm from the AIMD leads body distal end (FIG. 2C), and the placement of ferrite beads around 10 cm from the AIMD leads body distal end (FIG. 2D).

The different AIMD devices shown in FIGS. 2A-2D were placed inside an RF emission device for RF-induced heating measurements. Summaries of the device transfer functions are provided in Table 1 and FIGS. 3A-3D.

TABLE 1

| Use of ferrite materials to reduce RF-induced heating of AIMDs. | | |
|---|---|---|
| AIMD Conditions | 2 min ΔT (° C.) at 1.5 T | 2 min ΔT (° C.) at 3 T |
| Lead with no ferrite | 3.48 | 3.52 |
| Lead with ferrite 5 cm from tip | 1.12 | 0.94 |
| Lead with ferrite 10 cm from tip | 1.79 | 1.09 |

Figure 3A:
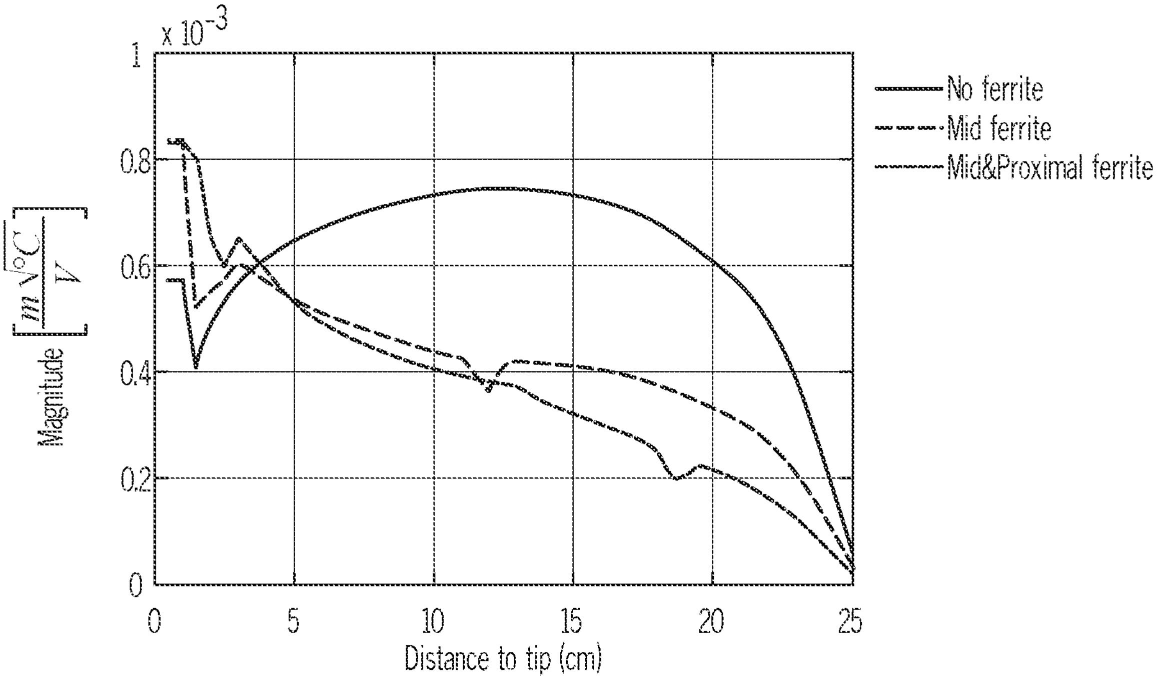
FIGS. 3A-3D show transfer functions of the AIMDs in FIGS. 2A-2D with and without ferrite materials.
Figure 3B:
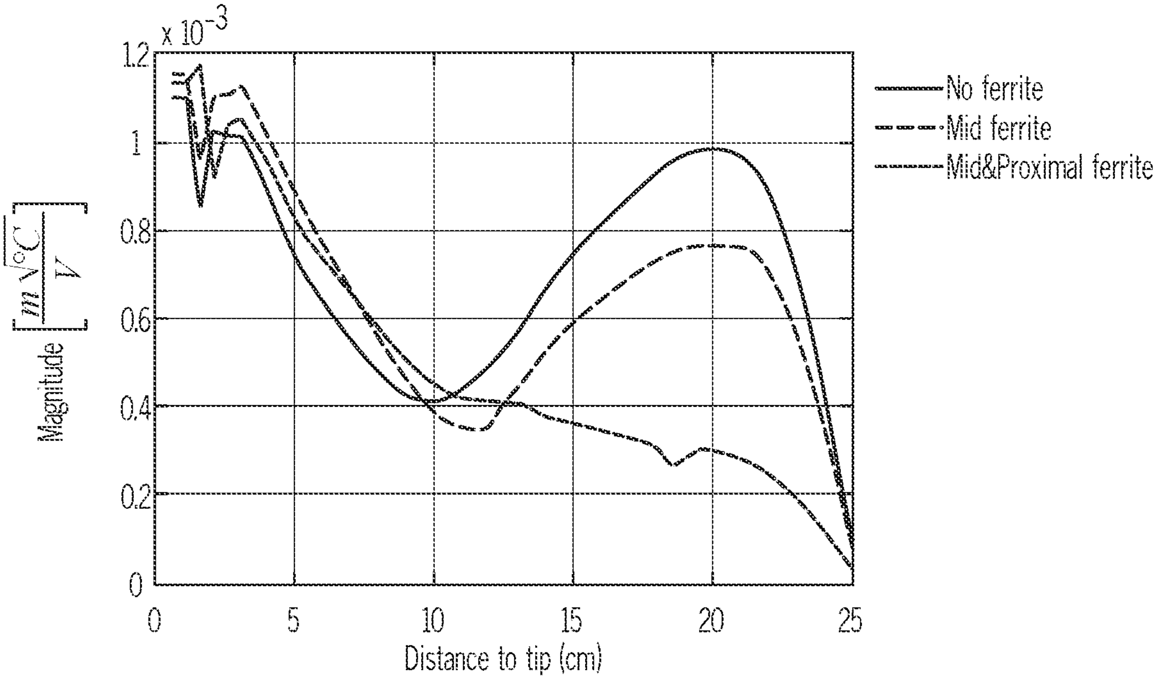
Figure 3C:
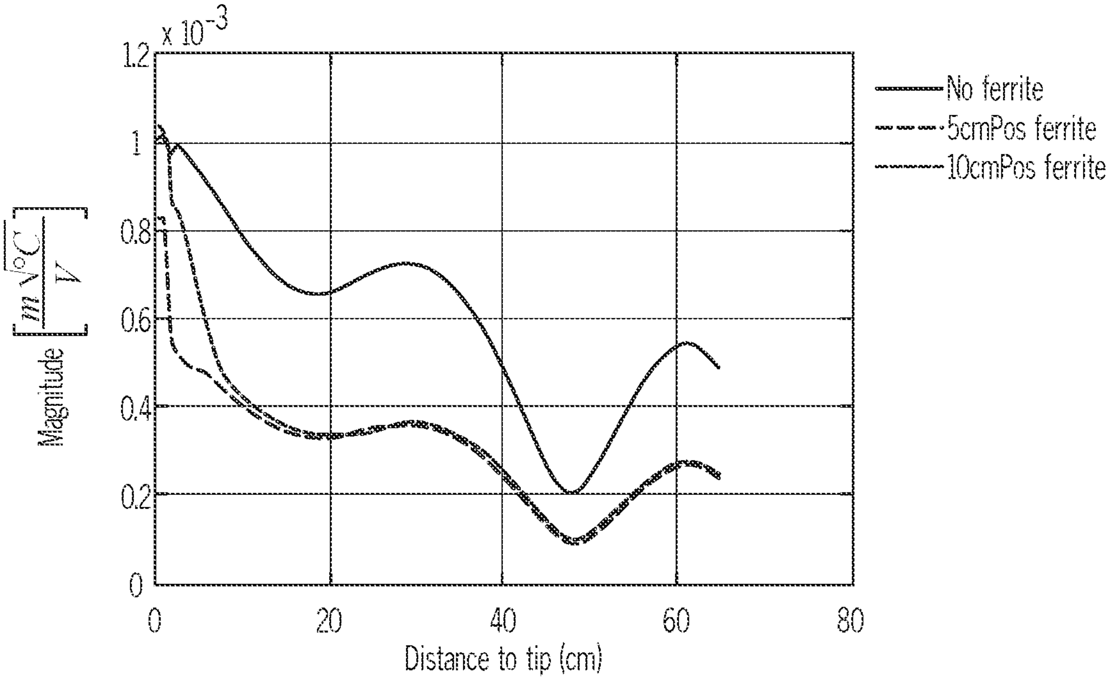
Figure 3D:
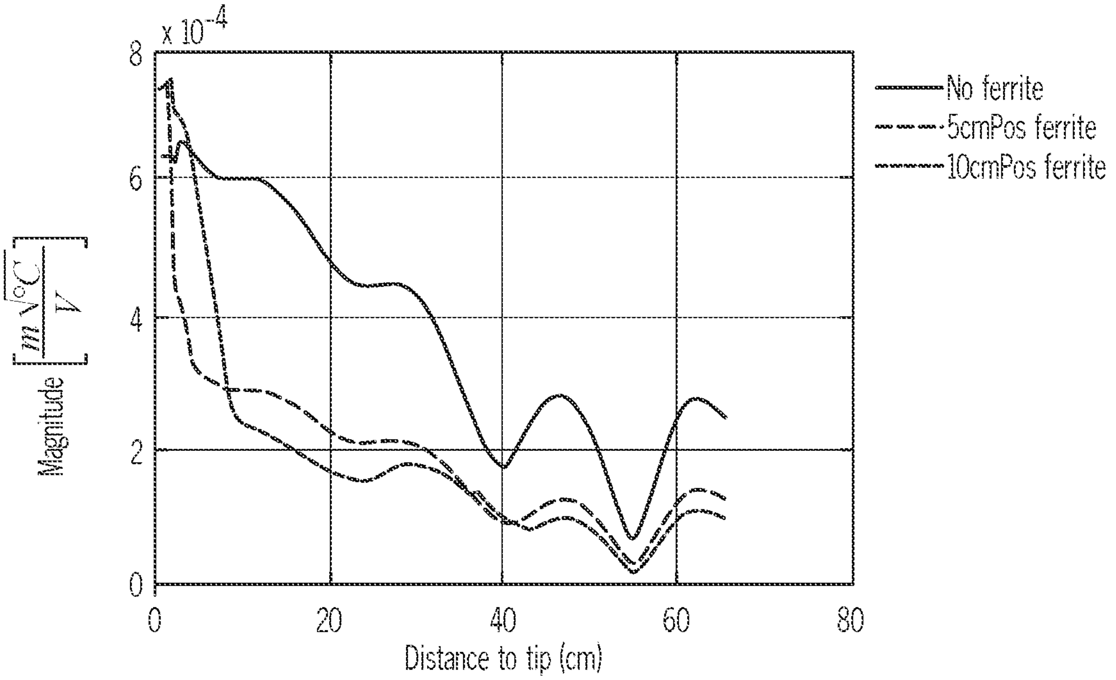

The results establish that the magnitude of the transfer functions of the AIMD models all decreased significantly when ferrite materials were applied along their leads bodies. In particular, FIGS. 3A and 3B show comparisons of transfer function models of AIMDs with and without ferrite materials at 1.5T (FIG. 3A) and 3T (FIG. 3B). The "Mid ferrite" and "Mid & Proximal ferrite" AIMDs represent the AIMDs in FIGS. 2A and 2B, respectively. FIGS. 3C and 3D show comparisons of transfer function models of AIMDs with and without ferrite materials at 1.5T (FIG. 3C) and 3T (FIG. 3D). The "5 cm Pos ferrite" and "10 cm Pos ferrite" AIMDs represent the AIMDs in FIGS. 2C and 2D, respectively.

In summary, the results in this Example demonstrate that ferrite materials can be utilized to reduce RF-induced heating of medical devices, such as AIMDs, by reducing the RF-induced current on the device.

Figure 4A:
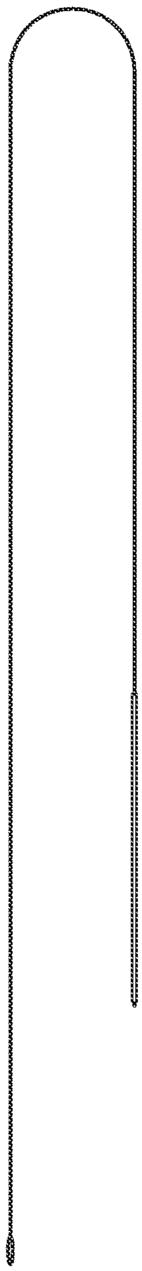
FIGS. 4A-4C illustrate the placement of ferrite materials on the leads body of an AIMD.
Figure 4B:
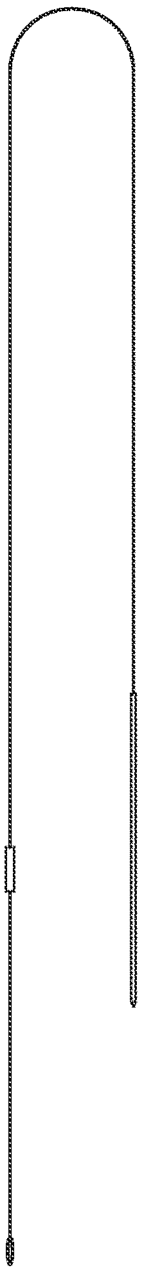
Figure 4C:
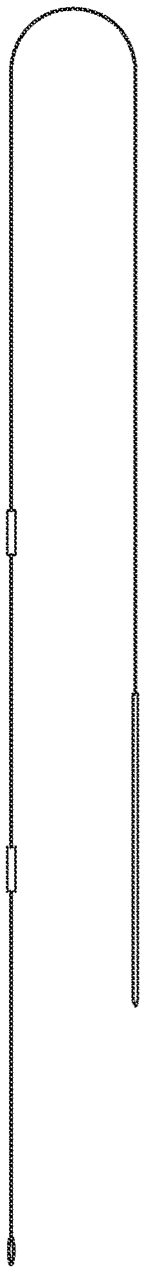

Example 2. Use of Ferrite Materials to Reduce RF-Induced Heating in Active Implantable Medical Devices This Example demonstrates the use of ferrite beads to reduce RF-induced heating of additional active implantable medical devices (AIMDs). Three different leads bodies, with and without the ferrite materials, were used in this Example. The device configurations are shown in FIGS. 4A-4C. Such configurations include a leads body with no ferrite beads (FIG. 4A), a leads body with a ferrite bead at about 11 cm from the distal tip (FIG. 4B), and a leads body with ferrite beads at about 11 cm and 21 cm from the distal tip (FIG. 4C).

Figure 5A:
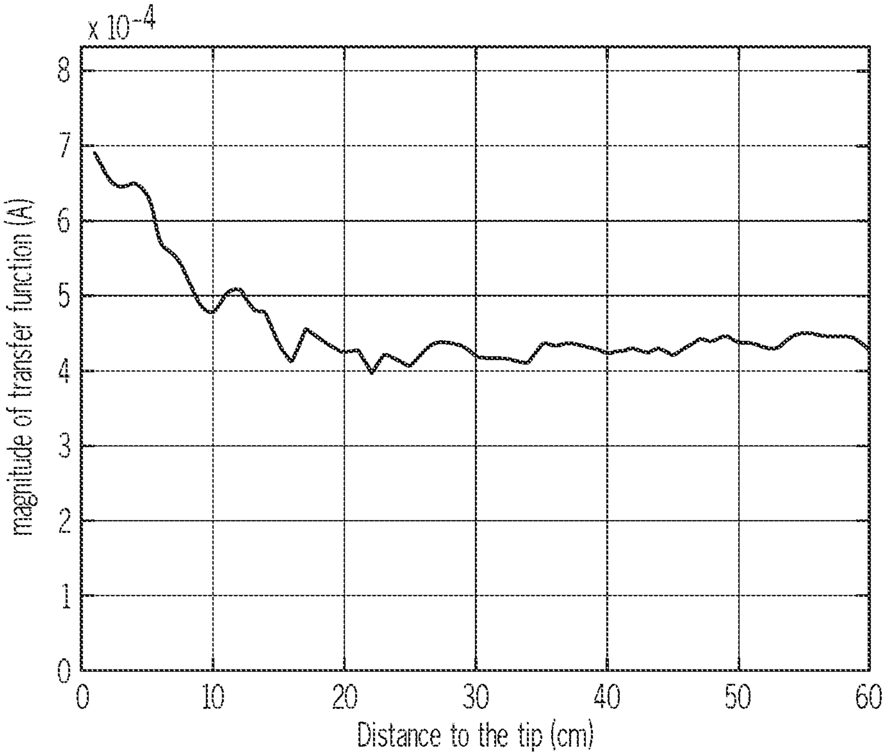
FIGS. 5A-5B show the heat transfer functions of the leads body in FIG. 4A at 1.5 T.
Figure 5B:
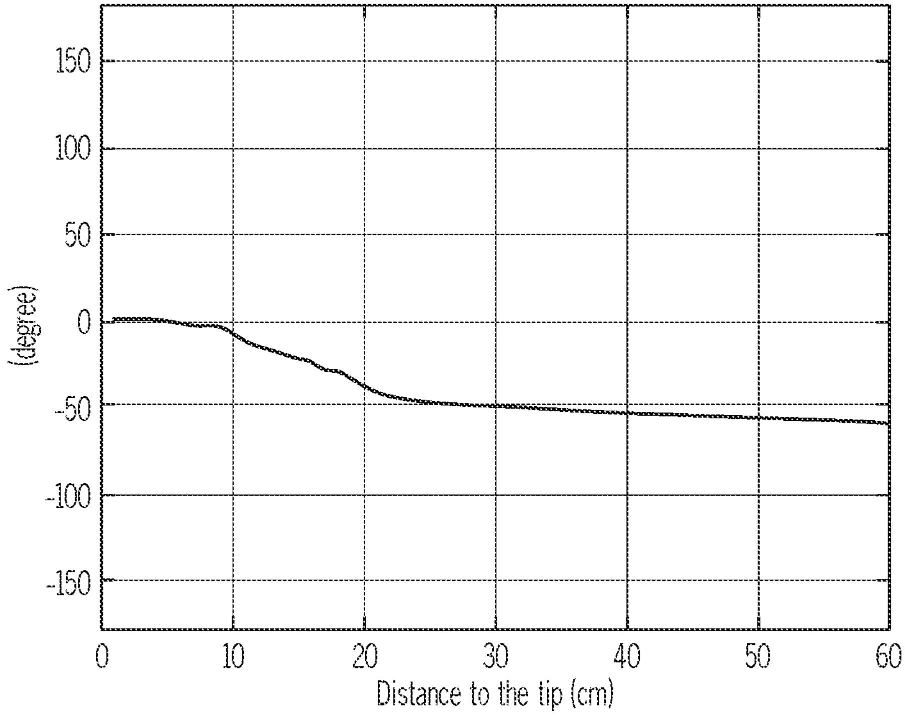
Figure 6A:
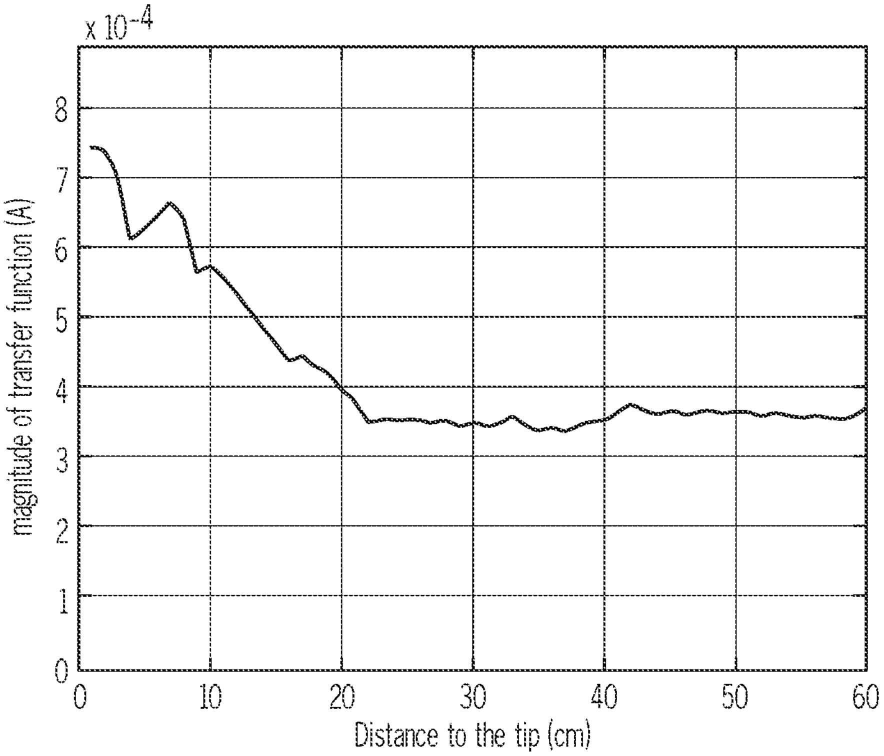
FIGS. 6A-6B show the heat transfer functions of the leads body in FIG. 4B at 1.5 T.
Figure 6B:
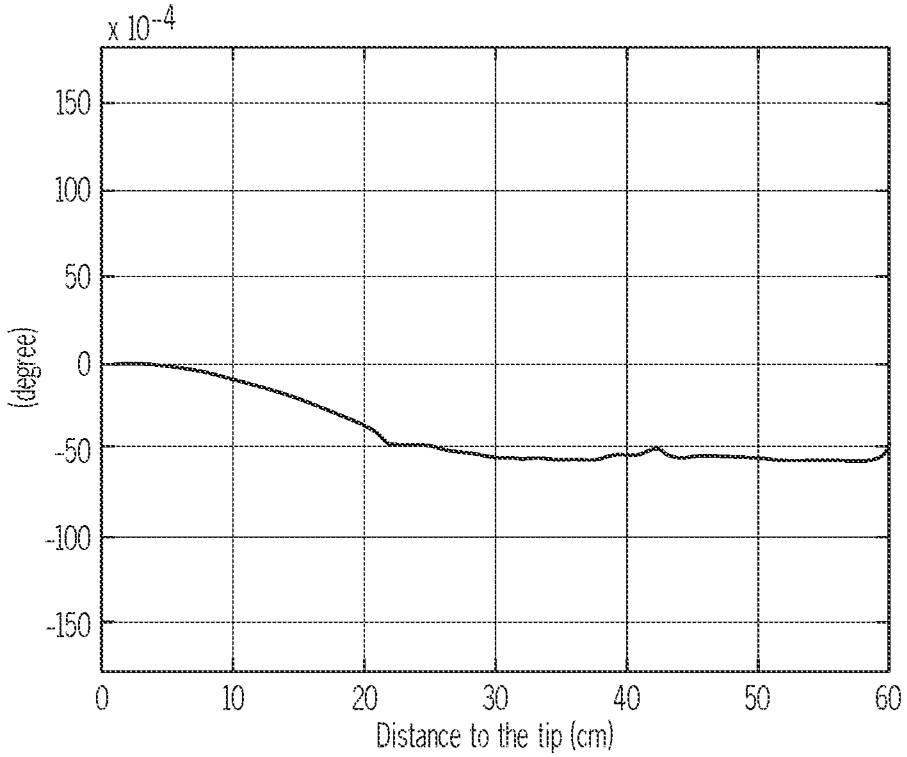
Figure 7A:
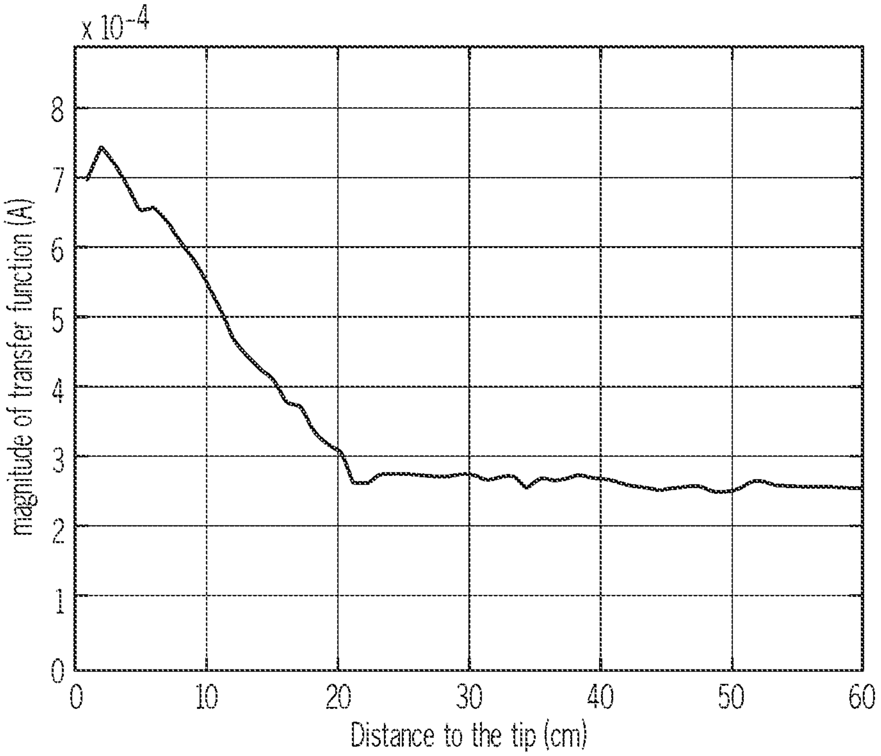
FIGS. 7A-7B show the heat transfer functions of the leads body in FIG. 4C at 1.5 T.
Figure 7B:
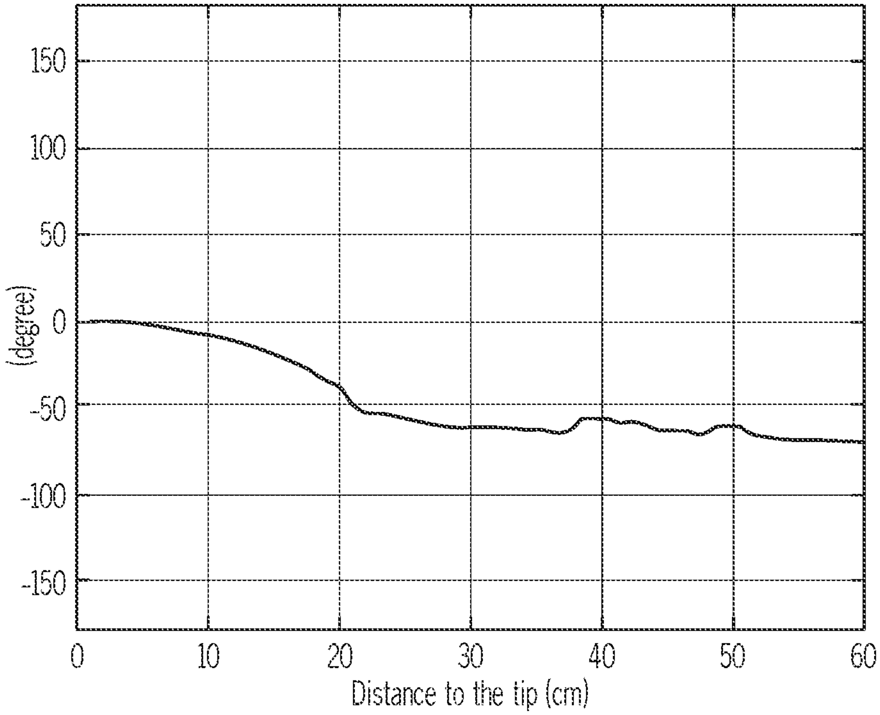
Figure 8A:
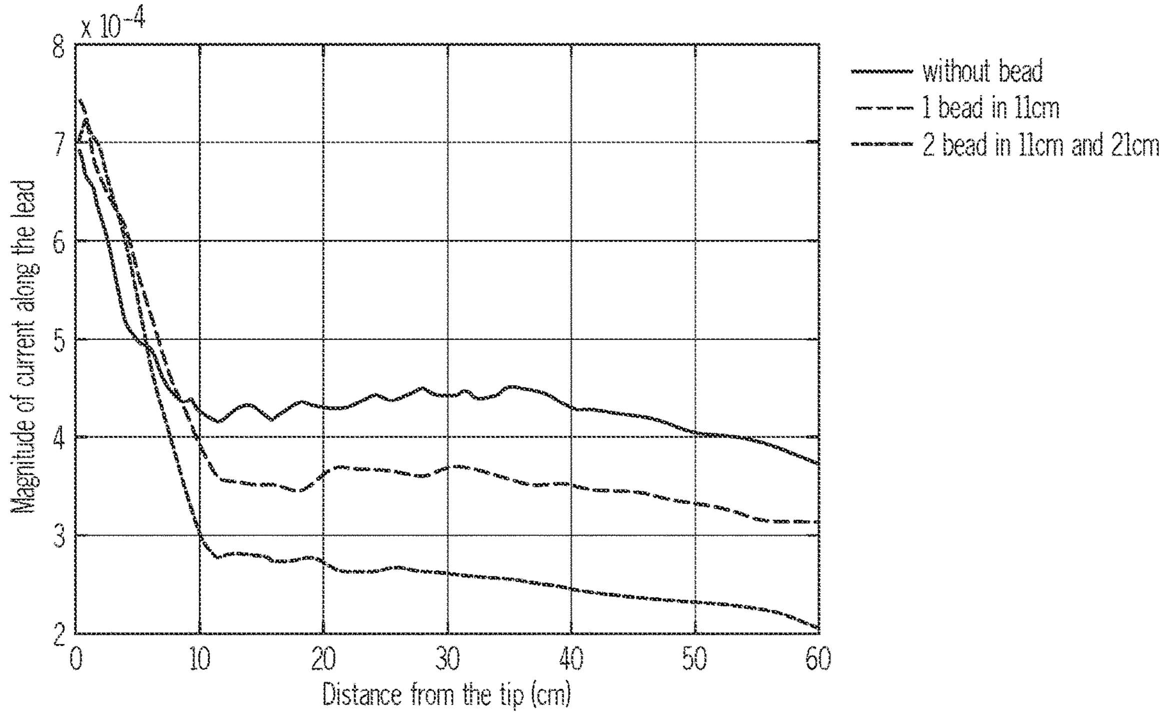
FIGS. 8A-8B show the heat transfer functions of the leads bodies in FIG. 4A-4C. The "without bead", "1 bead in 11 cm" and "2 beads in 11 cm and 21 cm" legends represent the AIMD leads bodies in FIGS. 4A, 4B, and 4C, respectively.
Figure 8B:
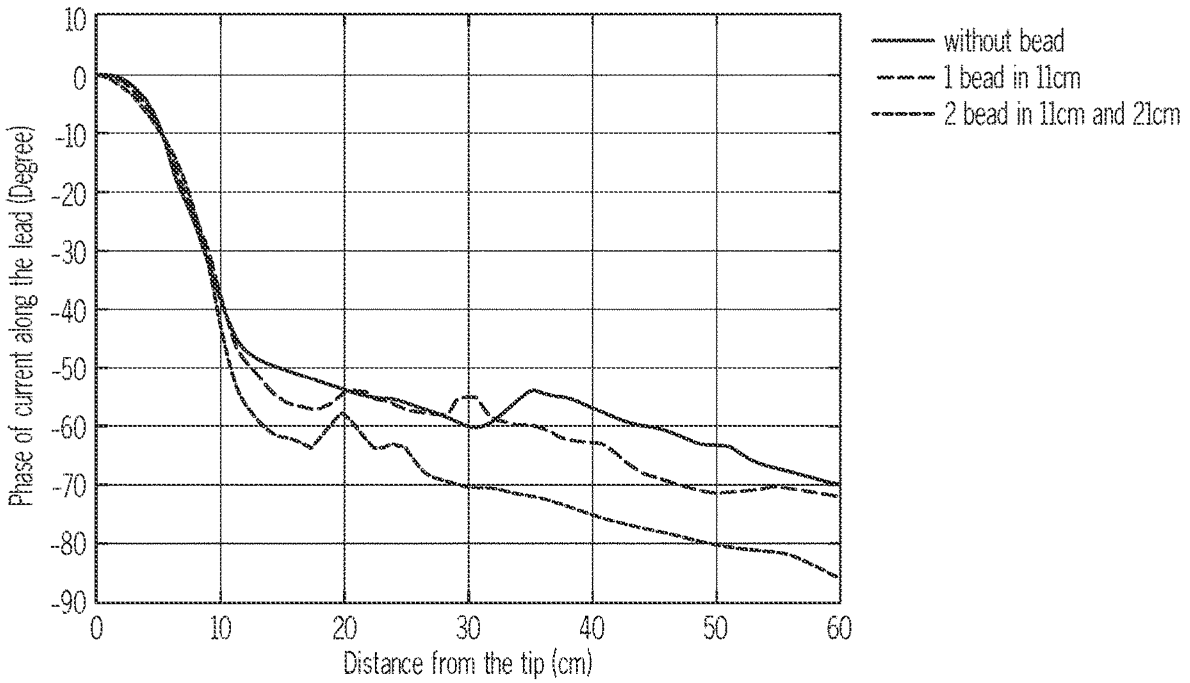
Figure 9A:
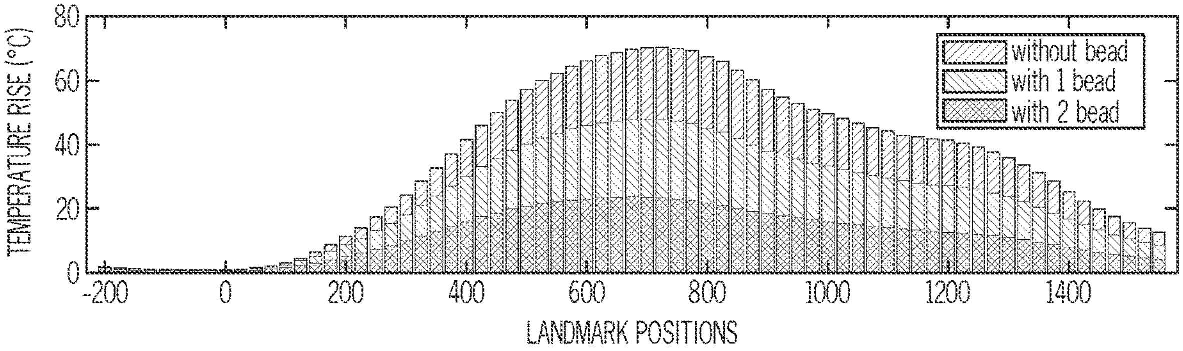
FIGS. 9A-9C show the heating results of the straight leads bodies in FIG. 4A-4C in different human models, including the adult Male model (Duke, 34 yrs, BMI 22.4, FIG. 9A) and the adult female model (Ella, 26 yrs, BMI 21.6, FIGS. 9B-9C). The "without bead", "with one bead" and "with one bead" legends represent the AIMD leads bodies in FIGS. 4A, 4B, and 4C, respectively.
Figure 9B:
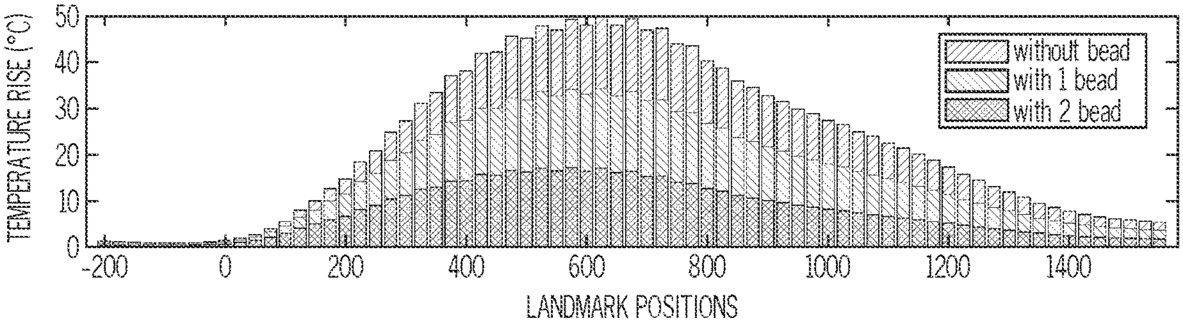
Figure 9C:
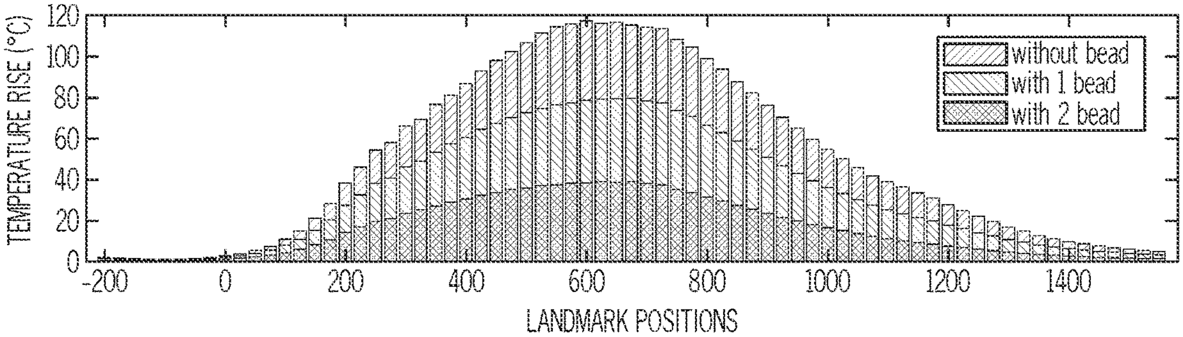
Figure 10A:
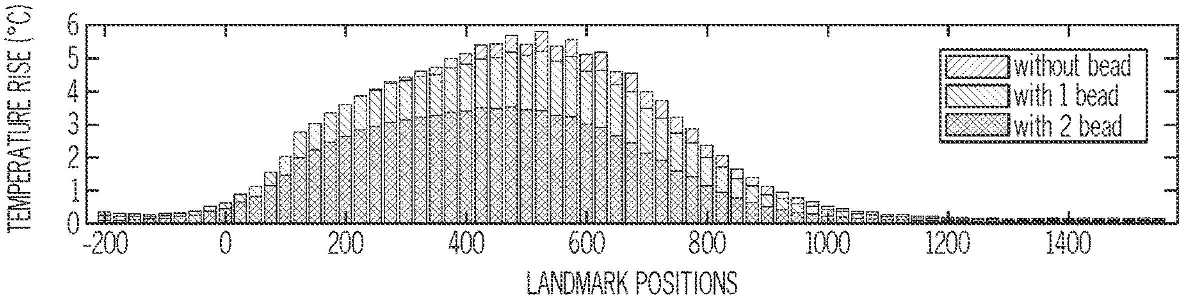
FIGS. 10A-10C show the heating results of the coiled leads bodies in FIG. 4A-4C in different human models, including the adult Male model (Duke, 34 yrs, BMI 22.4, FIG. 10A), the adult female model (Ella, 26 yrs, BMI 21.6, FIG. 10B), and the adult obese male model (Obese, 37 yrs, BMI 36.1, FIG. 10C). The "without bead", "with one bead" and "with one bead" legends represent the AIMD leads bodies in FIGS. 4A, 4B, and 4C, respectively.
Figure 10B:
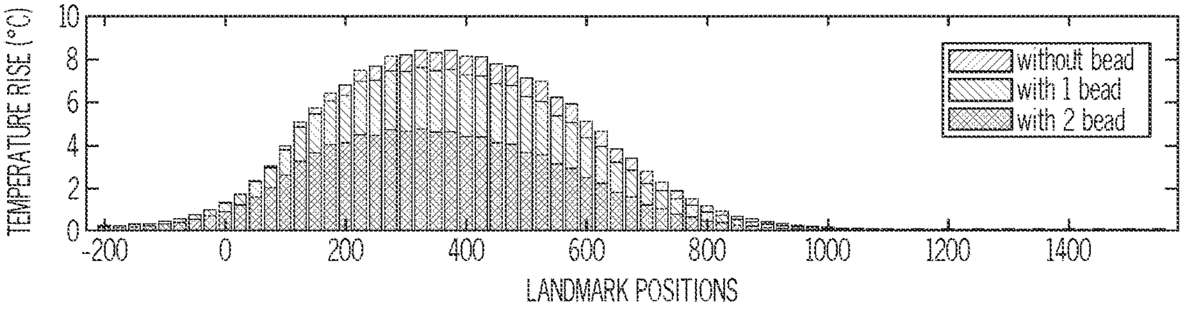
Figure 10C:
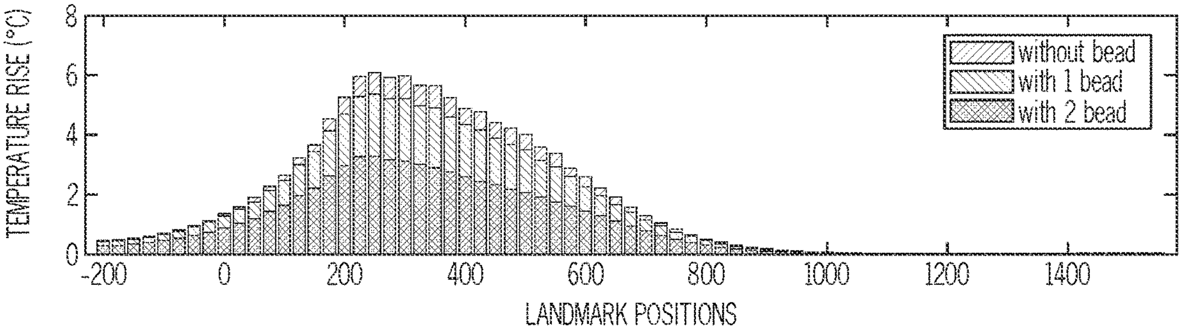

The different AIMD devices shown in FIGS. 4A-4C were placed inside an RF emission device for RF-induced heating measurements. Summaries of the device transfer functions are provided in Table 2, FIGS. 5A-5B, 6A-6B, 7A-7B, and 8A-8B. In particular, FIGS. 5A-5B show the heat transfer functions of the leads body in FIG. 4A at 1.5 T. FIGS. 6A-6B show the heat transfer functions of the leads body in FIG. 4B at 1.5 T. FIGS. 7A-7B show the heat transfer functions of the leads body in FIG. 4C at 1.5 T. FIGS. 8A-8B show the heat transfer functions of the leads bodies in FIG. 4A-4C.

TABLE 2

| Use of ferrite materials to reduce RF-induced heating of AIMDs. | | |
|---|---|---|
| AIMD Conditions | Heating for 2 minutes (° C.) | Heating for 30 minutes (° C.) |
| Lead with no ferrite | 15.7 | 24.10 |
| Lead with ferrite 11 cm from tip | 11.60 | 17.50 |
| Lead with ferrites 11 cm and 21 cm from tip | 6.50 | 8.90 |
| Rod (15 minutes) | 5.50 | N/A |

The results further confirm that the magnitude of the transfer functions of the AIMD models all decreased significantly when ferrite materials were applied along their leads bodies, and consequently, the RF-induced heating at the device tip can be reduced significantly.

As indicated in FIGS. 9A-9C and 10A-10C, when ferrite materials are used with the AIMD, the RF-induced heating is much lower in all human body models at all landmarks. A summary of the 95% heating values are listed in Table 3.

TABLE 3

| Use of ferrite materials to reduce RF-induced heating of AIMDs. | | | | | | |
|---|---|---|---|---|---|---|
| | Straight | | | Coiled | | |
| AIMD Conditions | Duke | Ella | Obese | Duke | Ella | Obese |
| Lead with no ferrite | 46.79 | 36.9 | 92.56 | 2.54 | 3.29 | 2.9 |
| Lead with ferrite 11 cm from tip | 32.03 | 25.31 | 61.68 | 2.49 | 3.01 | 2.41 |
| Lead with ferrites 11 cm and 21 cm from tip | 15.80 | 12.55 | 29.48 | 1.83 | 2.00 | 1.44 |

Figure 11B:
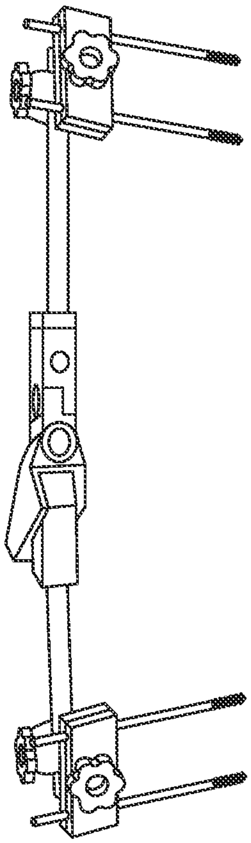
FIGS. 11A-D show configurations of different external fixation medical devices used in Example 3. The external fixation medical devices include External Fixator I without ferrite magnetic materials (FIG. 11A), External Fixator II without ferrite magnetic materials (FIG. 11B), External Fixator I with ferrite magnetic materials (FIG. 11C), and External Fixator II with ferrite magnetic materials (FIG. 11D).
Figure 11D:
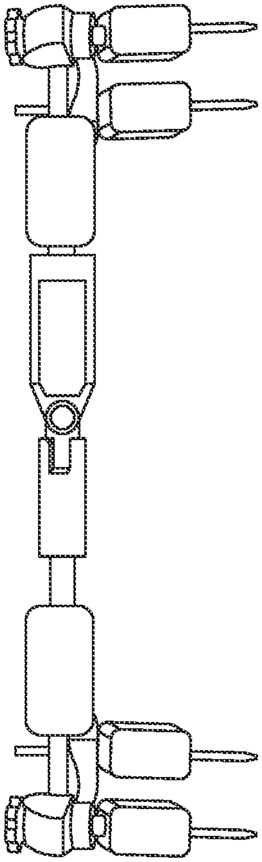
Figure 11A:
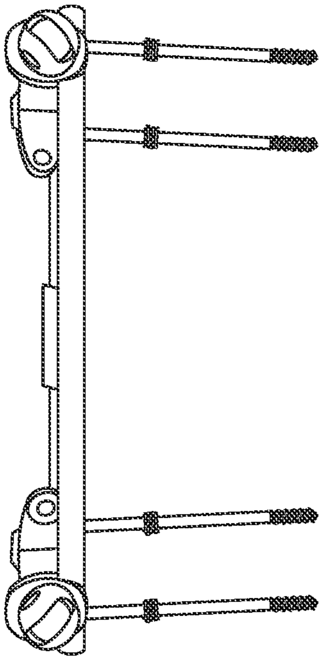
Figure 11C:
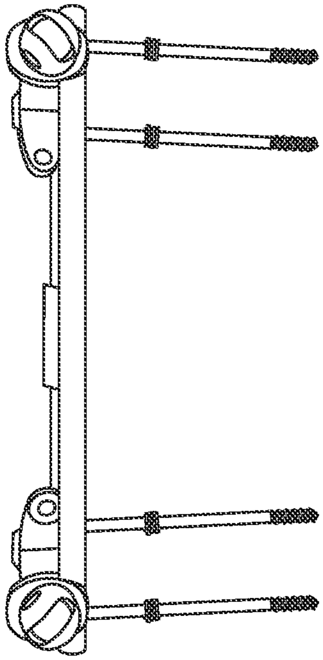

Example 3. Use of Ferrite Materials to Reduce RF-Induced Heating of External Fixation Medical Devices This Example demonstrates the use of ferrite beads to reduce RF-induced heating of external fixation medical devices. During experiments, the ASTM phantom with a commercially available external fixation device was tested as an example. Images of the external fixation medical devices tests in this Example are shown in FIGS. 11A-D. The external fixation medical devices include External Fixator I without ferrite magnetic materials (FIG. 11A), External Fixator II without ferrite magnetic materials (FIG. 11B), External Fixator I with ferrite magnetic materials (FIG. 11C), and External Fixator II with ferrite magnetic materials (FIG. 11D).

The different external fixation systems were placed under MR RF coil at 1.5 T. Optical-fiber thermal probes were used to measure the temperature rises near the pin tips. To hold the external fixation at the correct position, a plastic holder was used. For the temperature measurements, Applicant built the ASTM phantom with the following dimensions: 420 mm×180 mm×650 mm. The ASTM phantom was filled with GEL made of sodium chloride (NaCl, 1.32 g/L) and polyacrylic acid (10 g/L) dissolved in water. The phantom was filled with GEL to a depth of 90 mm. Based on the simulated results, the optical-fiber thermal probes were placed at the tips of the device pins. The total exposure time of the tested device in the RF field is 2 minutes at 1.5 T.

The results are summarized in Table 4. As summarized in Table 4, when external fixation devices are used, the RF-induced heating is reduced to background heating.

TABLE 4

| Use of ferrite materials to reduce RF-induced heating of external fixation medical devices. | | |
|---|---|---|
| | External Fixator I [° C.] | External Fixator II [° C.] |
| With ferrite materials | 0.91 | 0.43 |
| Without ferrite materials | 2.53 | 3.25 |

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. An implantable medical device operational for mitigating radiofrequency (RF)-induced heating, wherein the implantable medical device comprises:

a ferrite material associated with at least one component of the implantable medical device, wherein the at least one component of the implantable medical device comprises an electrode that is partially or completely implantable into the subject, wherein the ferrite material represents an exogenous component of the medical device that protrudes out of the at least one component of the medical device, and wherein the ferrite material is operational to reduce the RF-induced heating of the implantable medical device.

2. The implantable medical device of claim 1, wherein the ferrite material comprises iron oxide ($Fe_2O_3$) combined with one or more additional metallic elements, wherein the one or more metallic elements comprise iron (Fe), strontium (Sr), barium (Ba), manganese (Mn), nickel (Ni), zinc (Zn), cobalt (Co), and combinations thereof.

3. The implantable medical device of claim 1, wherein the ferrite material is selected from the group consisting of strontium (Sr)-containing ferrites, barium (Ba)-containing ferrites, manganese (Mn)-containing ferrites, nickel (Ni)-containing ferrites, zinc (Zn)-containing ferrites, cobalt (Co)-containing ferrites, Ni, Zn-containing ferrites, Mn, Zn-containing ferrites, magnetite ($Fe_3O_4$), $ZnFe_2O_4$, $BaFe_{12}O_{19}$ ($BaO{:}6Fe_2O_3$), $BaO\cdot 2(FeO)\cdot 8(Fe_2O_3)$, $SrFe_{12}O_{19}$ ($SrO{:}6Fe_2O_3$), $MnZnFe_2O_4$, $NiZnFe_2O_4$, $CoFe_2O_4$ ($CoO\cdot Fe_2O_3$), $Ba_2ZnFe_{18}O_{23}$, and combinations thereof.

4. The implantable medical device of claim 1, wherein the ferrite material is associated with an outer surface of the at least one component of the implantable medical device.

5. The implantable medical device of claim 1, wherein the implantable medical device comprises an active implantable medical device (AIMD).

6. The implantable medical device of claim 1, wherein the implantable medical device comprises an external fixation medical device.

7. The implantable medical device of claim 1, wherein the implantable medical device comprises an active implantable medical device (AIMD), wherein the at least one component of the implantable medical device comprises a lead body of the AIMD.

8. The implantable medical device of claim 1, wherein the implantable medical device comprises an external fixation medical device, wherein the at least one component of the implantable medical device comprises a fixator of the external fixation medical device.

9. A method of mitigating radiofrequency (RF)-induced heating of an implantable medical device, said method comprising:

applying a ferrite material to at least one component of an implantable medical device, wherein the at least one component of the implantable medical device comprises an electrode that is partially or completely implantable into the subject, wherein the ferrite material represents an exogenous component of the medical device that protrudes out of the at least one component of the medical device, and wherein the ferrite material reduces the RF-induced heating of the medical device.

10. The method of claim 9, wherein the ferrite material comprises iron oxide ($Fe_2O_3$) combined with one or more additional metallic elements, wherein the one or more metallic elements comprise iron (Fe), strontium (Sr), barium (Ba), manganese (Mn), nickel (Ni), zinc (Zn), cobalt (Co), and combinations thereof.

11. The method of claim 9, wherein the ferrite material is selected from the group consisting of strontium (Sr)-containing ferrites, barium (Ba)-containing ferrites, manganese (Mn)-containing ferrites, nickel (Ni)-containing ferrites, zinc (Zn)-containing ferrites, cobalt (Co)-containing ferrites, Ni, Zn-containing ferrites, Mn, Zn-containing ferrites, magnetite ($Fe_3O_4$), $ZnFe_2O_4$, $BaFe_{12}O_{19}$ ($BaO{:}6Fe_2O_3$), $BaO\cdot 2(FeO)\cdot 8(Fe_2O_3)$, $SrFe_{12}O_{19}$ ($SrO{:}6Fe_2O_3$), $MnZnFe_2O_4$, $NiZnFe_2O_4$, $CoFe_2O_4$ ($CoO\cdot Fe_2O_3$), $Ba_2ZnFe_{18}O_{23}$, and combinations thereof.

12. The method of claim 9, wherein the ferrite material is applied to an outer surface of the at least one component of the implantable medical device.

13. The method of claim 9, wherein the implantable medical device comprises an external fixation medical device.

14. The method of claim 9, wherein the implantable medical device comprises an active implantable medical device (AIMD).

15. The method of claim 9, wherein the at least one component of the implantable medical device is partially or completely implantable into the subject.

16. The method of claim 9, wherein the implantable medical device comprises an active implantable medical device (AIMD), wherein the at least one component of the implantable medical device comprises a lead body of the AIMD.

17. The method of claim 9, wherein the implantable medical device comprises an external fixation medical device, wherein the at least one component of the implantable medical device comprises a fixator of the external fixation medical device.

18. The method of claim 9, wherein the ferrite material reduces RF-induced heating by blocking or minimizing the induced current from RF waves.

19. The method of claim 9, wherein the ferrite material mitigates RF-induced heating in an environment comprising magnetic resonance.

20. The method of claim 9, further comprising a step of implanting the implantable medical device into a subject.

21. A method of mitigating radiofrequency (RF)-induced heating of an implantable medical device, said method comprising:

applying a ferrite material to at least one component of an implantable medical device, wherein the ferrite material represents an exogenous component of the medical device that protrudes out of the at least one component of the medical device, and wherein the ferrite material reduces the RF-induced heating of the medical device; and implanting the implantable medical device into a subject, wherein the implanting comprises completely implanting the implantable medical device into the subject.

22. The method of claim 20, wherein the implanting comprises partially or completely implanting the implantable medical device into the subject.

23. The method of claim 20, wherein the implanting occurs after the applying step.

24. The method of claim 20, wherein the subject is a human being.

25. The implantable medical device of claim 1, wherein the ferrite material is in a form selected from the group consisting of rings, beads, blocks, or combinations thereof.

26. The method of claim 9, wherein the ferrite material is in a form selected from the group consisting of rings, beads, blocks, or combinations thereof.

* * * * *